(12) United States Patent
Tokumaru

(10) Patent No.: US 10,041,033 B2
(45) Date of Patent: Aug. 7, 2018

(54) CULTURE APPARATUS

(71) Applicant: PHC HOLDINGS CORPORATION, Tokyo (JP)

(72) Inventor: Tomoyoshi Tokumaru, Gunma (JP)

(73) Assignee: PHC HOLDINGS CORPORATION, Tokyo (JP)

(*) Notice: Subject to any disclaimer, the term of this patent is extended or adjusted under 35 U.S.C. 154(b) by 166 days.

(21) Appl. No.: 15/065,562

(22) Filed: Mar. 9, 2016

(65) Prior Publication Data
US 2016/0186114 A1 Jun. 30, 2016

Related U.S. Application Data

(63) Continuation of application No. PCT/JP2014/077156, filed on Oct. 10, 2014.

(30) Foreign Application Priority Data

Oct. 11, 2013 (JP) ................... 2013-214060

(51) Int. Cl.
*C12M 1/12* (2006.01)
*C12M 1/00* (2006.01)
*C12M 3/00* (2006.01)

(52) U.S. Cl.
CPC ............ *C12M 25/06* (2013.01); *C12M 23/46* (2013.01); *C12M 23/48* (2013.01); *C12M 41/14* (2013.01)

(58) Field of Classification Search
CPC ...... C12M 25/06; C12M 23/16; C12M 23/18; C12M 41/14; B01L 9/523; B01L 1/025; B01L 2200/141
See application file for complete search history.

(56) References Cited

U.S. PATENT DOCUMENTS

| | | | |
|---|---|---|---|
| 2009/0194089 A1* | 8/2009 | Durney | B21D 11/10 126/19 R |
| 2010/0167383 A1 | 7/2010 | Busujima et al. | |
| 2012/0083030 A1 | 4/2012 | Busujima et al. | |

FOREIGN PATENT DOCUMENTS

| CN | 1616647 A | 5/2005 |
|---|---|---|
| EP | 2180037 A1 | 4/2010 |

(Continued)

OTHER PUBLICATIONS

Lin, Mu, et al., Jun. 3, 2010, "Sheet Metal Forming Technology and Mold Design," The BJ University Press (Peking University), pp. 1-4 with cover sheet.

(Continued)

*Primary Examiner* — Michael L Hobbs
(74) *Attorney, Agent, or Firm* — McDermott Will & Emery LLP

(57) ABSTRACT

A culture apparatus comprises an outer case, an inner case configured with two side plates, a bottom plate and a top plate, and arranged inside the outer case, a door configured to open and close an opening formed in a front face of the inner case, and a plurality of shelves. Each of the side plates include raised portions vertically arranged and formed by press working. The raised portions of the side plates constitute plural pairs of shelf rests. Each of the raised portions includes an upper face as a placement portion, on which one of the plurality of shelves is to be placed, and a lower face. A stopper portion which limits movement in a vertical direction of a shelf placed on an immediately lower pair of shelf rests is provided on the lower face and protrudes from the lower face by the press working.

12 Claims, 18 Drawing Sheets

(56) References Cited

FOREIGN PATENT DOCUMENTS

| EP | 2423626 A2 | 2/2012 |
| EP | 2573162 A1 | 3/2013 |
| JP | 2004-000275 A | 1/2004 |
| JP | 2004-222731 A | 8/2004 |
| JP | 2006-071281 A | 3/2006 |
| JP | 2010-051218 A | 3/2010 |
| JP | 2010-057398 A | 3/2010 |
| JP | 2012-075373 A | 4/2012 |

OTHER PUBLICATIONS

Qi, Li, et al., Nov. 31, 2008, "Mold Design and Manufactuing," The PeopleCharts Telecon Publishing House (Posts & Telecom Press), pp. 1-3 with cover sheet.

The Second Office Action issued in corresponding Chinese Patent Application No. 201480050532.4, dated Feb. 9, 2017; with English translation.

English Translation of Chinese Office Action issued in Chinese Application No. 201480050532.4 dated Aug. 17, 2016.

International Search Report issued in Application No. PCT/JP2014/077156 dated Dec. 16, 2014, with English translation.

* cited by examiner

CULTURE APPARATUS

CROSS-REFERENCE TO RELATED APPLICATIONS

This is a continuation application of International Patent Application No. PCT/JP2014/077156 filed Oct. 10, 2014, which claims the benefit of priority to Japanese Patent Application No. 2013-214060 filed Oct. 11, 2013. The full contents of the International Patent Application are incorporated herein by reference.

BACKGROUND

The present disclosure relates to a culture apparatus.

DESCRIPTION OF THE RELATED ART

For example, a culture apparatus configured to cultivate culture is known (for example, Japanese Patent Application Laid-Open Publication No. 2010-51218).

For example, in a culture apparatus in Japanese Patent Application Laid-Open Publication No. 2010-51218 includes, in the inside thereof, supports for holding a shelf on which culture is to be placed. Thus, for example, the supports may interfere with cleaning of the interior of the culture apparatus, resulting in cleaning being insufficient. Further, the number of components is increased by an amount equal to the number of the supports, which may cause complicated work in cleaning the interior of the culture apparatus.

SUMMARY

A culture apparatus configured to cultivate cultures, the culture apparatus comprising: an outer case; an inner case configured with two side plates, a bottom plate and a top plate, all of which are metal plates, the inner case being arranged inside the outer case; a door configured to open and close an opening formed in a front face of the inner case; and a plurality of shelves on which the cultures are to be placed, wherein: the side plates include plural pairs of shelf rests formed by press working, each of the plural pairs of shelf rests includes stoppers formed by press working, each of the plurality of shelves includes side parts on both sides of bottom surfaces, the side parts being configured to be placed on one of the pairs of shelf rests in such a manner that the plurality of shelves are arranged in a vertical direction, the stoppers are provided such that the stoppers of one pair of shelf rests limit movement in a vertical direction of a shelf placed on an immediately lower pair of shelf rests, each of the plurality of shelf rests includes a placement surface, on which one of the shelves is to be placed, and an inclined surface formed on undersides of the placement surface, and the stoppers are provided, below the placement surface, on the inclined surface.

Other features of the present invention will become apparent from descriptions of the present specification and of the accompanying drawings.

BRIEF DESCRIPTION OF THE DRAWINGS

For more thorough understanding of the present invention and advantages thereof, the following description should be read in conjunction with the accompanying drawings.

DETAILED DESCRIPTION

At least the following details will become apparent from descriptions of the present specification and of the accompanying drawings.

First Embodiment

===Culture Apparatus===

Figure 1:
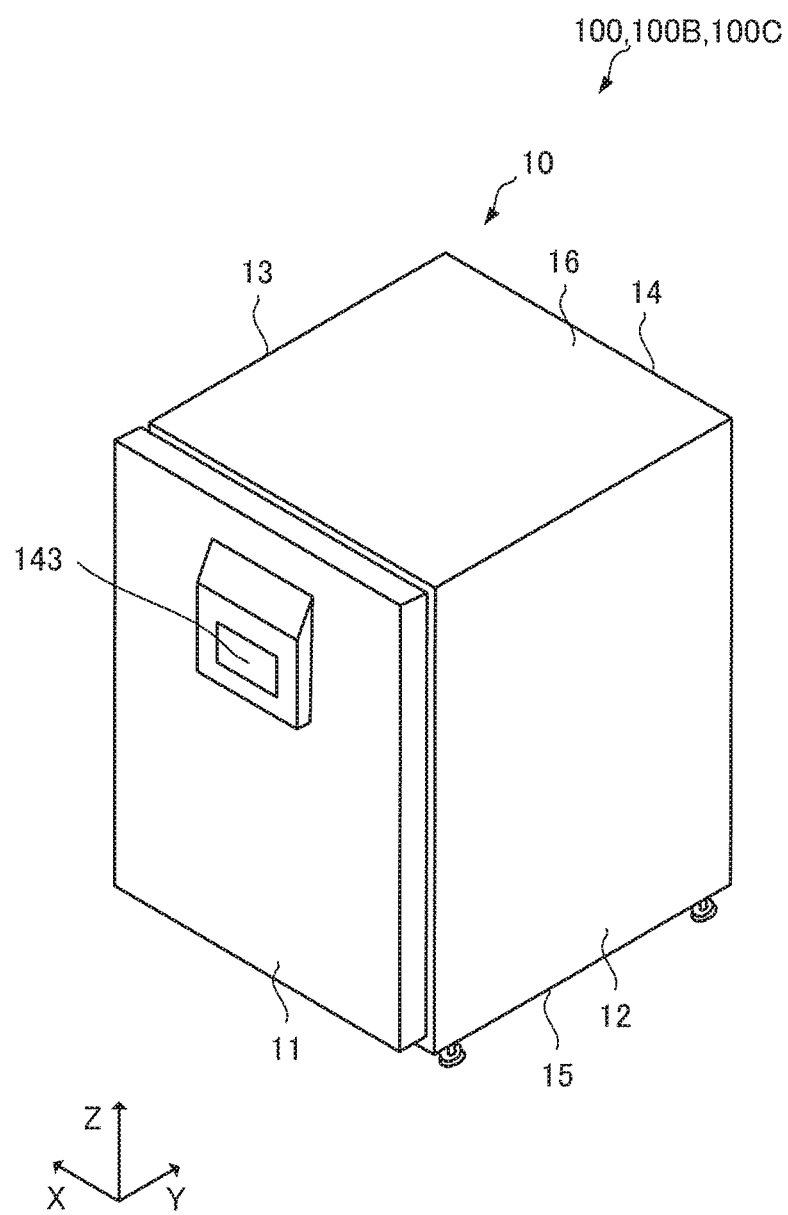
FIG. 1 is a perspective view illustrating a culture apparatus according to first to third embodiments.
Figure 2:
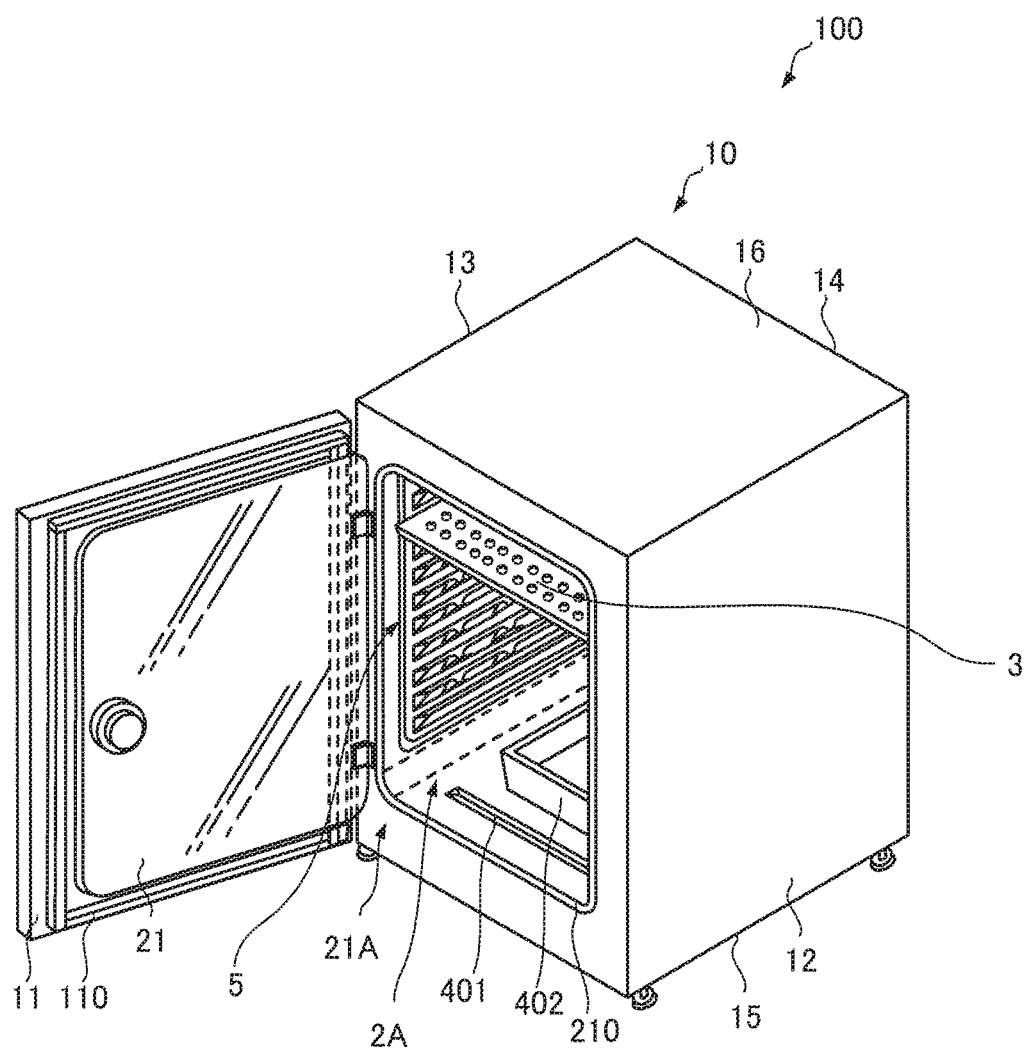
FIG. 2 is a perspective view illustrating the culture apparatus in a state where an outer door and an inner door thereof are opened according to the first embodiment.
Figure 3:
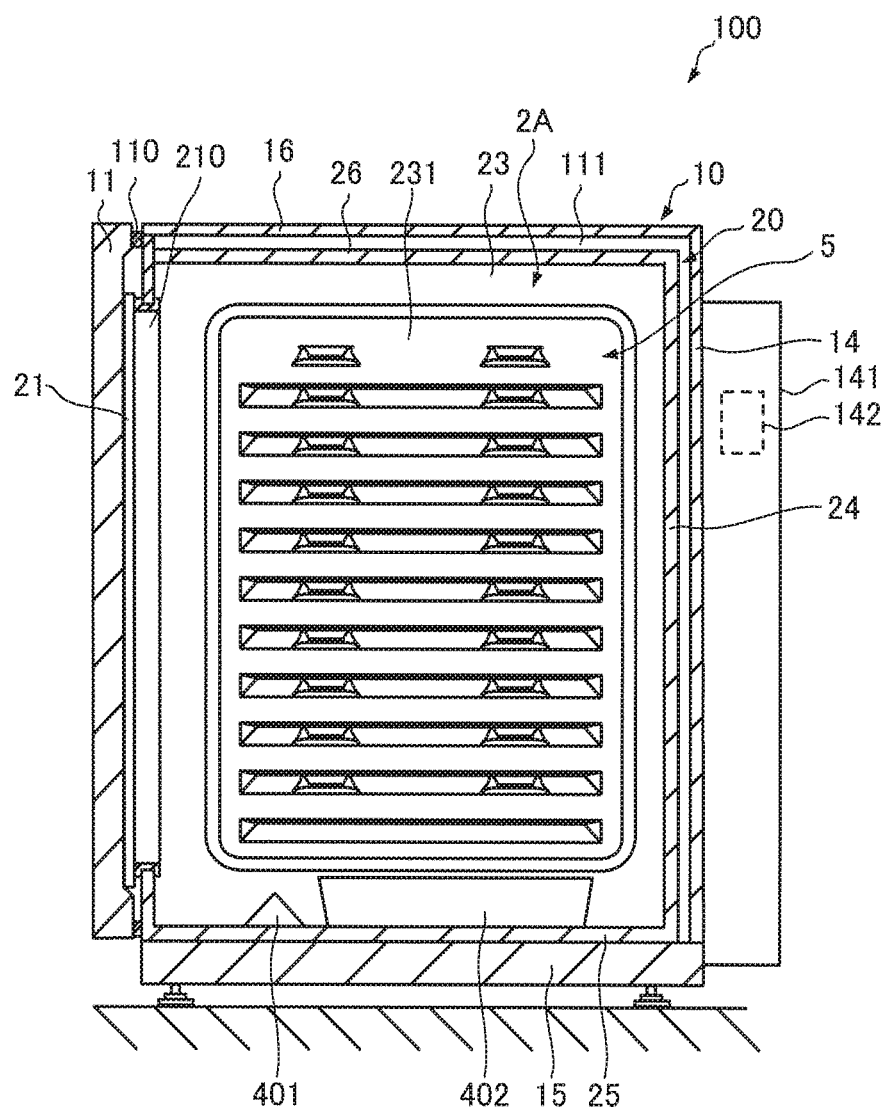
FIG. 3 is a cross-sectional view illustrating the culture apparatus according to the first embodiment.
Figure 4:
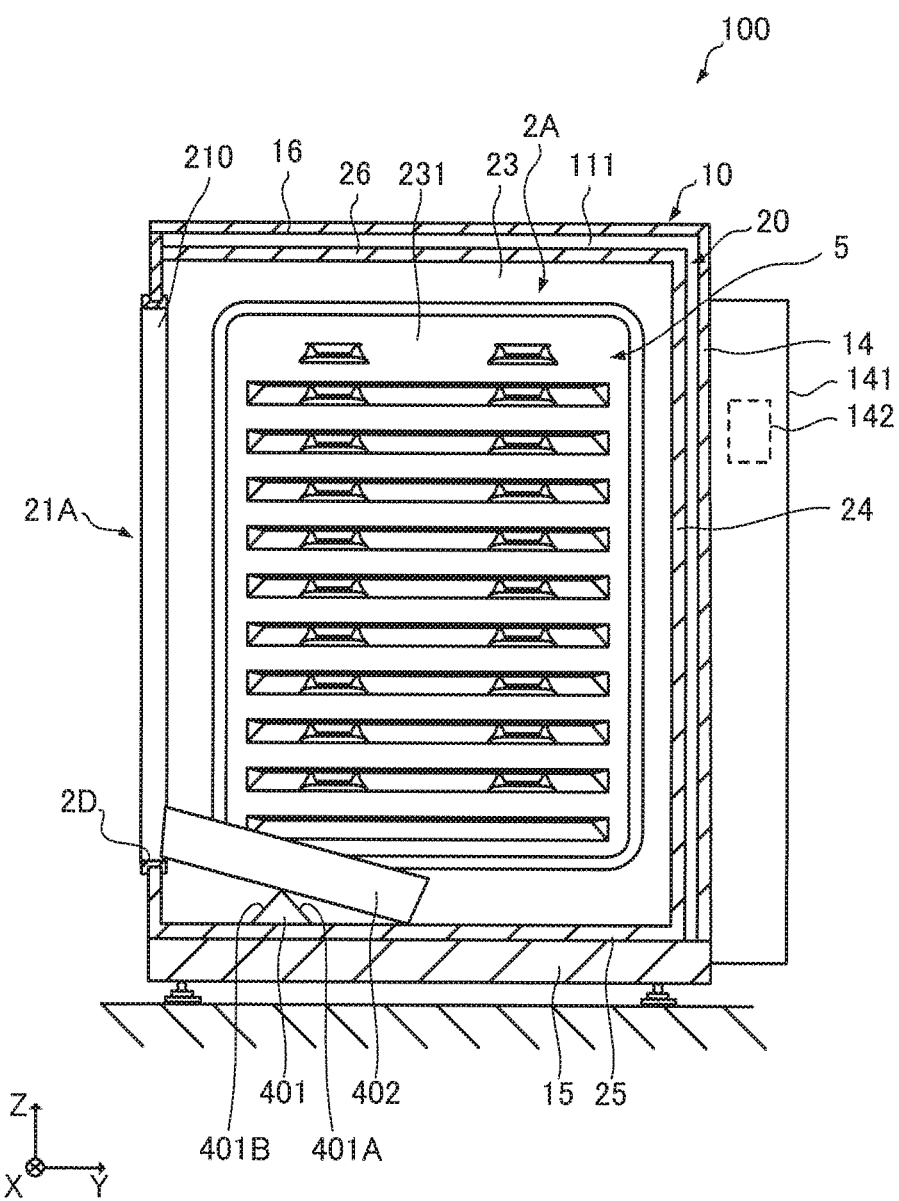
FIG. 4 is a cross-sectional view illustrating the culture apparatus in a state where the outer door thereof is omitted, according to the first embodiment.

Hereinafter, a culture apparatus according to an embodiment of the present disclosure will be described with reference to FIGS. 1 to 4. FIG. 1 is a perspective view illustrating the culture apparatus according to the present embodiment. FIG. 2 is a perspective view illustrating the culture apparatus in a state where an outer door and an inner door thereof are opened according to the present embodiment. FIG. 3 is a cross-sectional view illustrating the culture apparatus according to the present embodiment. FIG. 4 is a cross-sectional view illustrating the culture apparatus in a state where the outer door is omitted according to the present embodiment. FIGS. 3 and 4 illustrate the culture apparatus 100 when viewed from a cross-section, parallel to a ZY plane, passing through substantially the center of the culture apparatus 100.

Note that an X-axis is an axis orthogonal to side plates 12, 13 of an outer case 10, and it is assumed that a direction from the side plate 12 toward the side plate 13 is a +X direction and a direction from the side plate 13 toward the side plate 12 is a −X direction. A Y-axis is an axis orthogonal to an outer door 11 and a back plate 14, and it is assumed that a direction from the outer door 11 toward the back plate 14 is a +Y direction and a direction from the back plate 14 toward the outer door 11 is a −Y direction. A Z-axis is an axis orthogonal to a bottom plate 15 and a top plate 16, and it is assumed that an up direction from the bottom plate 15 toward the top plate 16 is a +Z direction and a down direction from the top plate 16 toward the bottom plate 15 is a −Z direction.

The culture apparatus 100 is a device configured to perform culture of a body to be cultured, such as cells, microorganisms, etc., within a culture chamber 2A. The culture apparatus 100 includes: the outer case 10; the outer door 11; an inner case 20 (FIG. 3); an inner door 21, a water tray 402, a shelf 3, and a heater device 142 (FIG. 3).

The outer case 10 and the inner case 20 are a substantially rectangular parallelepiped box body that is made of metal material such as stainless steel, etc. The external form of the inner case 20 is smaller than the internal form of the outer case 10 such that the inner case 20 is housed inside the outer case 10. A space 111 (FIG. 3) filled with air which exerts an effect of thermal insulation is formed between the inner case 20 and the outer case 10. Note that the space 111 may be filled with predetermined thermal insulation other than air. An opening 21A leading to the culture chamber 2A is formed in a front surface (−Y) of the outer case 10 and the inner case 20.

The outer door 11 and the inner door 21 are doors configured to open/close the opening 21A. The outer door 11 is made of a metal material, such as stainless steel, etc., is of a substantially rectangular shape greater than the outer form of the inner door 21, and is filled with thermal insulation in the interior thereof. A gasket 110 for securing airtightness inside the culture apparatus 100 is provided in the periphery of the outer door 11 on the side adjacent to the inner door 21. An operating device 143 configured to operate the culture apparatus 100 is provided to the outer door 11 on the side opposite to the inner door 21. The inner door 21 is a member made of a transparent material such as resin, glass, etc. A gasket 210 for securing airtightness inside the culture apparatus 100 is provided to a part, to be opposed to and come into contact with the inner door 21, in an edge of the opening 21A of the outer case 10. Note that a part 2B extending along the vertical direction of the gasket 210 on the side plate 13 side and a part 2C thereof on the side plate 12 side correspond to side parts on both sides of the opening 21A.

The shelf 3 is in a substantially rectangular shape when viewed from a +Z side toward a −Z side, and is made of a metal material such as stainless steel, etc., where a body to be cultured is to be placed. Further, the shelf 3 is to be placed on each of plural pair of shelf rests 5, 6 provided inside the inner case 20. Note that the single shelf 3 may be provided inside the inner case 20 or the plurality of shelves 3 may be provided.

The water tray 402 is a container in which water generated when dehumidifying the culture chamber 2A is to be stored, and placed on a bottom plate 25 of the inner case 20.

The heater device 142 is a device configured to adjust temperature in the culture chamber 2A and is provided in a case 141.

===Inner Case===

Figure 5:
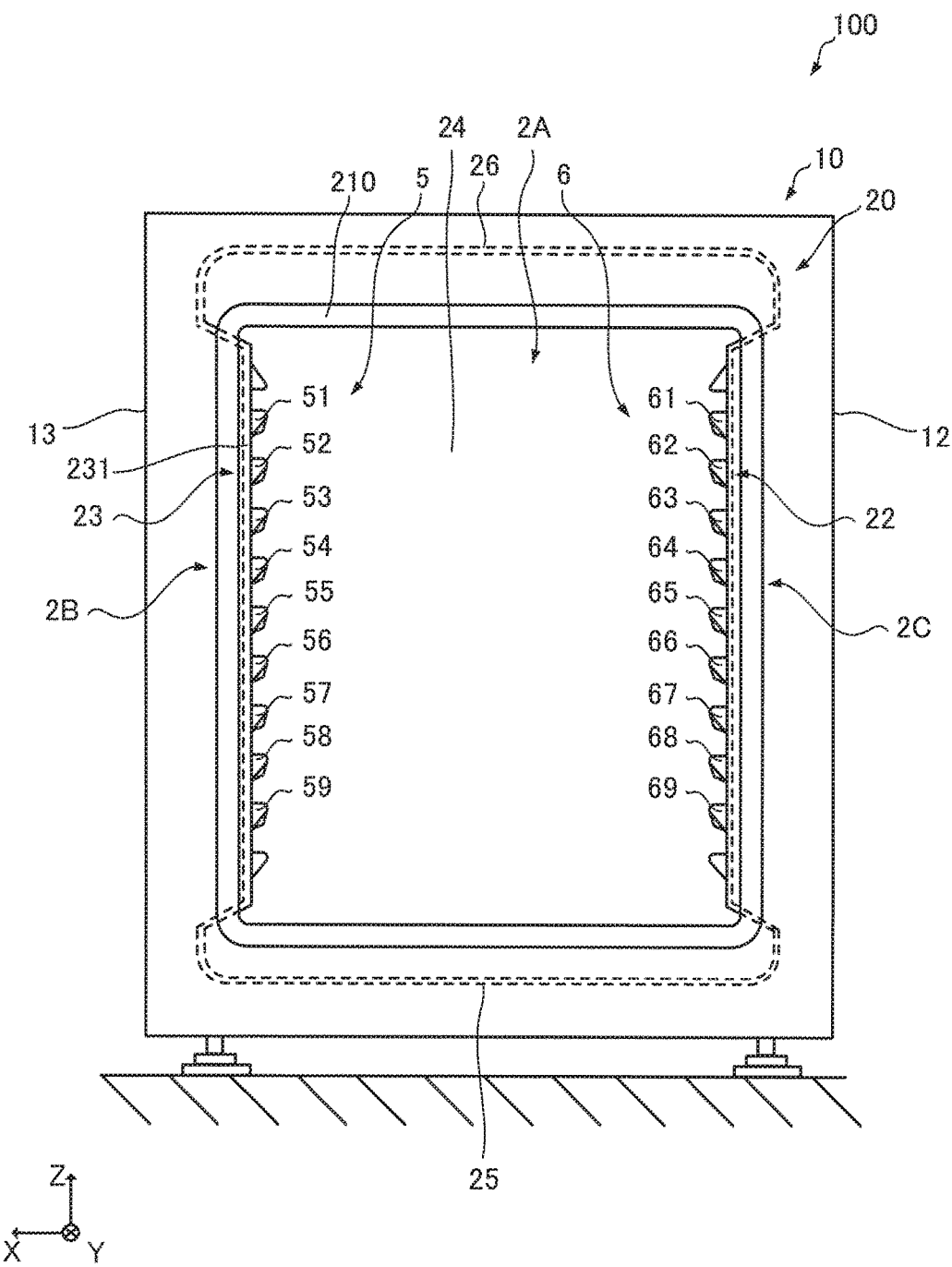
FIG. 5 is a front view illustrating the culture apparatus in a state where the outer door and the inner door are omitted according to the first embodiment.
Figure 6:
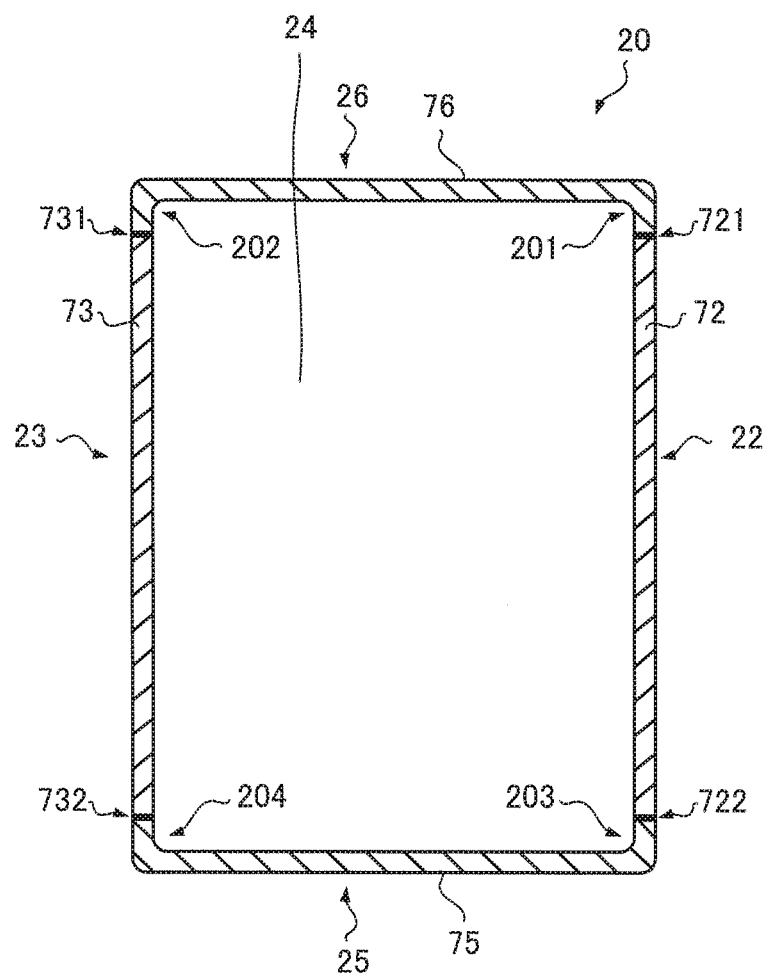
FIG. 6 is a cross-sectional view illustrating the inner case according to the first embodiment.
Figure 6:
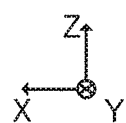

Hereinafter, the inner case according to the present embodiment will be described with reference to FIGS. 3, 5, and 6. FIG. 5 is a front view illustrating the culture apparatus in a state where the outer door and the inner door are omitted according to the present embodiment. FIG. 6 is a cross-sectional view illustrating the inner case according to the present embodiment. Note that FIG. 6 illustrates the inner case 20 when viewed from a cross-section parallel to a ZX-plane passing through substantially the center of the culture apparatus 100 in FIG. 1 toward the +Y direction. Further, for explanation's sake, side plates 22, 23, a back plate 24, the bottom plate 25, and a top plate 26 in the inner case 20 are illustrated as plane plates, respectively.

The inner case 20 includes: the side plates 22, 23, the back plate 24, the bottom plate 25, and the top plate 26. The side plates 22, 23, the bottom plate 25, and the top plate 26 are formed by welding four metal plates 72, 73, 75, and 76. The metal plates 72, 73 are plate members that are formed into the side plates 22, 23, for example, by being pressed so that the plurality of shelf rests 5, 6 are provided in the inner case 20. The metal plate 76 is a plate member to form the top plate 26. The metal plate 76 has its ends on both sides thereof bent such that joint parts 721, 731 are positioned closer to the side plates 22, 23 than corner parts 201, 202 of the substantially rectangular parallelepiped shape of the inner case 20. The metal plate 75 is a plate member to form the bottom plate 25. The metal plate 75 has its both ends bent such that joint parts 722, 732 are positioned closer to the side plates 22, 23 than corner parts 203, 204 of the substantially rectangular parallelepiped shape of the inner case 20.

The ends on both sides of the metal plate 76 are welded to the upper ends (+Z) of the metal plates 72, 73 at the joint parts 721, 731, respectively. The ends on both sides of the metal plate 75 are welded to the lower ends (−Z) of the metal plates 72, 73 at the joint parts 722, 732, respectively. The back surface plate 24 is welded to the edges on a +Y-side of the metal plates 72, 73, 75, and 76. Accordingly, the inner case 20 is formed.

===Interior of Inner Case===

Figure 7:
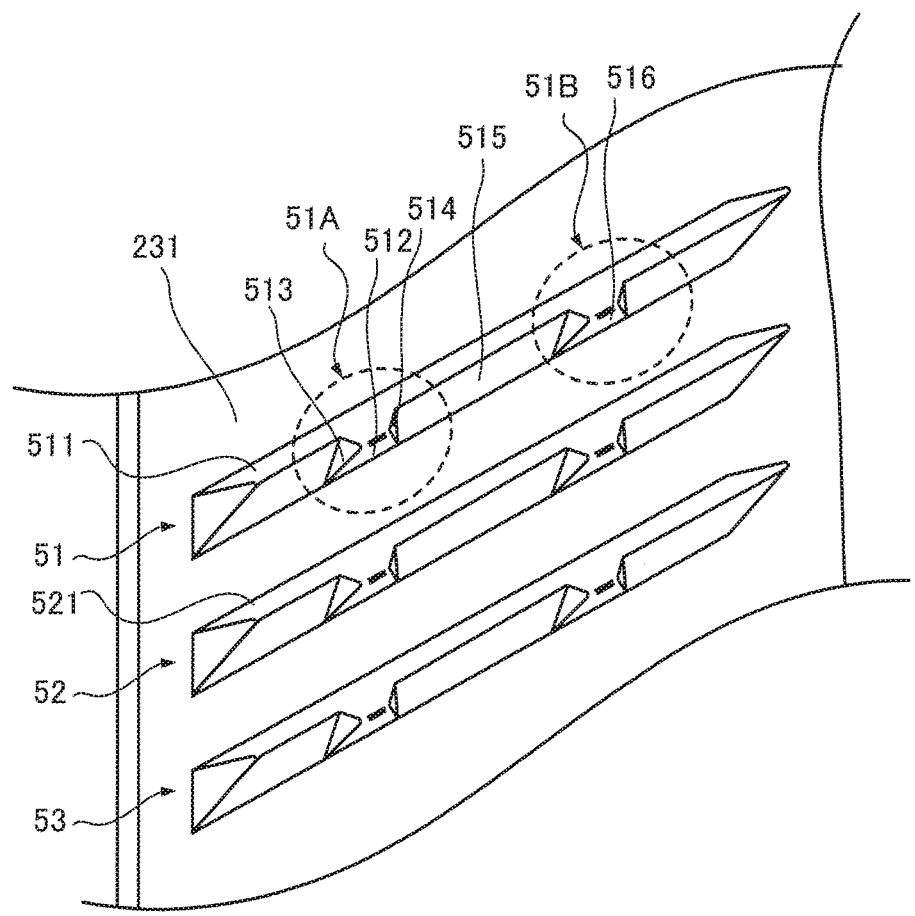
FIG. 7 is a perspective view illustrating shelf rests according to the first embodiment.
Figure 8:
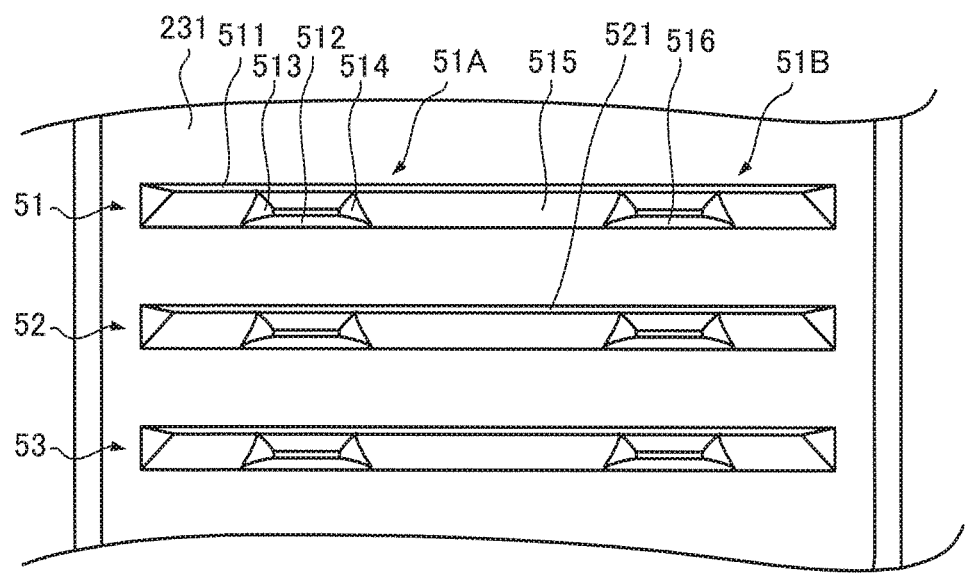
FIG. 8 is a front view illustrating the shelf rests according to the first embodiment.
Figure 9:
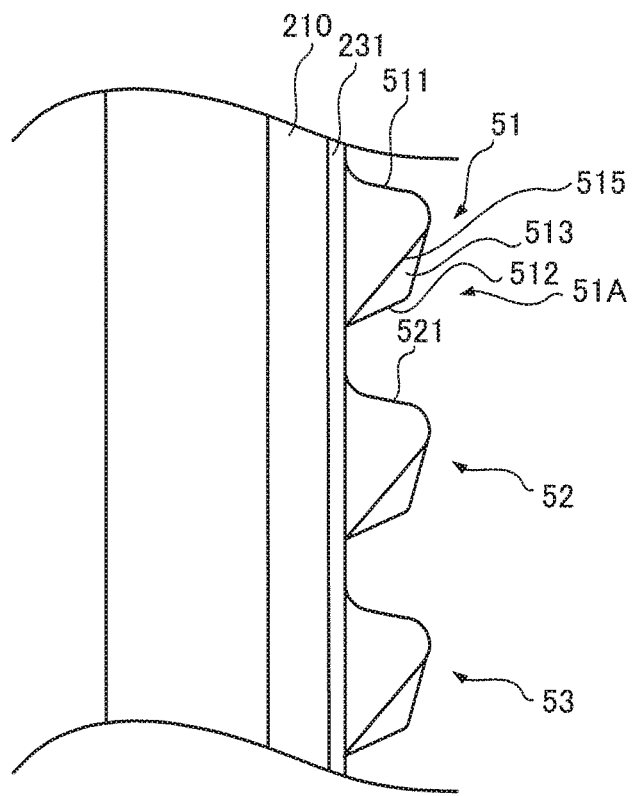
FIG. 9 is a side view illustrating the shelf rests according to the first embodiment.
Figure 10:
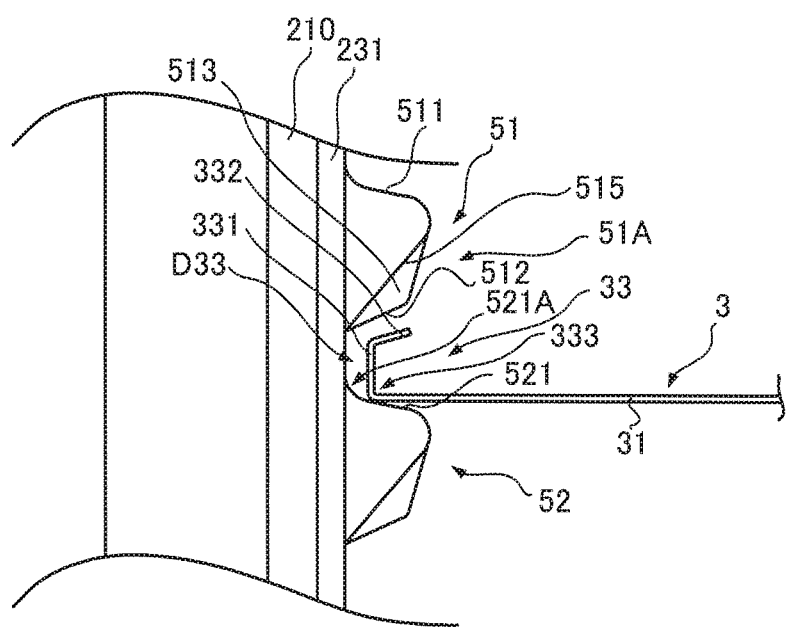
FIG. 10 is a side view illustrating the shelf rests in a state where a shelf is placed, according to the first embodiment.

Hereinafter, the interior of the inner case according to the present embodiment will be described with reference to FIGS. 4, 5, and 6 to 10. FIG. 7 is a perspective view illustrating the shelf rests according to the present embodiment. FIG. 8 is a front view illustrating the shelf rests according to the present embodiment. FIG. 9 is a side view illustrating the shelf rests according to the present embodiment. FIG. 10 is a side view illustrating the shelf rests in a state where the shelf is placed according to the present embodiment.

The interior of the inner case 20 is in a shape symmetrical with respect to a symmetry plane which passes through the center of the inner case 20 as well as is parallel to a YZ plane. In the interior of the inner case 20, the corners thereof are chamfered so as to facilitate cleaning.

=Shelf Rest=

The shelf 3 is placed on the plurality of shelf rests 5, 6. Each respective pair of shelf rests 51 to 59 in the plurality of shelf rests 5 and shelf rests 61 to 69 in the plurality of shelf rests 6 supports the shelf 3 in a manner such that the shelf 3 will become substantially horizontal. Note that since the shelf rests 51 to 59 of the plurality of shelf rests 5 have a construction similar to that of the shelf rests 61 to 69 of the plurality of shelf rests 6, only the plurality of shelf rests 5 will be described and the description of the plurality of shelf rests 6 is omitted.

The side plate 23 is subject to press working, to form the plurality of shelf rests 5. The plurality of shelf rests 5 are provided in a rising portion 231 in the side plate 23. The rising portion 231 configure a part of the side plate 23 that has been subjected to press working so as to rise in a direction (−X) away from the side plate 13 of the outer case 10. The rising portion 231 rises closer to the center of the inner case 20 (−X) than the gasket 210 (FIG. 9) serving as the edge of the opening 21A. Accordingly, the shelf 3 placed on the plurality of shelf rests 5 is securely positioned.

The plurality of shelf rests 5 include the shelf rests 51 to 59 provided in such a manner as to be arranged in the vertical direction (Z-axis). A distance between, for example, the shelf rest 51 serving as the shelf rest on the upper side (+Z) and the shelf rest 52 serving as the shelf rest on the lower side (−Z), which are immediately adjacent to each other in the vertical direction, is set at such a distance that a movement in the vertical direction of the shelf 3 placed on the shelf rest 52 is limited to a predetermined amount. Note that the predetermined amount corresponds to, for example, a certain distance, with which the shelf 3 can be moved in the front-back (Y-axis) direction in a state of being lifted up in the vertical direction, and may be, for example, about several millimeters or several centimeters. Note that since the shelf rests 51 to 59 have similar constructions to one another, only the shelf rest 51 will be described, and the descriptions of constructions of the shelf rests 52 to 59 are omitted.

The shelf rest 51 protrudes in a direction away from the side plate 13 of the outer case 10 and has a long shape continually extending from the inner door 21 side (−Y) to the back plate 24 side (+Y). The shelf rest 51 includes a placement surface 511, an inclined surface 515, and stoppers 51A, 51B.

A side part 33 in a bottom plate 31 of the shelf 3 is placed on the placement surface 511. The placement surface 511 may be formed to be substantially horizontal, thereby causing the placed shelf 3 to become horizontal, but as illustrated in the figure, the placement surface 511 is inclined toward the bottom plate 25 as it goes away (−X) from the side plate 23 of the inner case 20. Even though the shelf 3 is placed on this inclined placement surface 511, a construction is such that the placed shelf 3 is substantially centered, due to its own weight and the shapes of a bend of the shelf and a bend of a placement surface, which will be described later, and thereby the placed shelf 3 will become horizontal.

The inclined surface 515 is inclined downward (−Z) as well as toward the side plate 23 from the top of the shelf rest 51, such that the volume of the culture chamber 2A is increased. Note that the top of the shelf rest 51 is a part of the shelf rest 51 corresponding to a position farthest from the side plate 23 in an X-axis direction. The inclined surface 515 is provided downward (−Z) from the placement surface 511. Then, the thickness between the placement surface 511 and the inclined surface 515 in the vertical direction decreases as a distance from the side plate 23 increases.

The stoppers 51A, 51B are provided in such a manner integrated into the shelf rest 51, so as to limit the movement in the vertical direction of the shelf 3 that is placed on the shelf rest 51. The stoppers 51A, 51B are provided, at positions apart from each other, along the longitudinal direction (Y-axis) of the shelf rest 51. Since the stoppers 51A, 51B have constructions similar to each other, only the stopper 51A will be described and the description of the stopper 51B is omitted.

The stopper 51A is provided, to the inclined surface 515, downward (−Z) from the placement surface 511. The stopper 51A includes a first inclined surface 512, a second inclined surface 513, and a third inclined surface 514.

The first inclined surface 512 comes into contact with the side part 33 of the shelf 3, to limit the movement of the shelf 3 in the vertical direction. The first inclined surface 512 is provided lower than the inclined surface 515 (FIG. 9). The first inclined surface 512 is inclined such that an inferior angle formed between the first inclined surface 512 and the side plate 23 becomes greater than an inferior angle formed between the inclined surface 515 and the side plate 23. The second inclined surface 513 is inclined so as to prevent the shelf 3 from being blocked by the stopper 51A when the shelf 3 is inserted into the inner case 20. The second inclined surface 513 is inclined toward the +Y direction as a distance from the side plate 23 increases. The third inclined surface 514 is inclined so as to prevent the shelf 3 from being blocked by the stopper 51A when the shelf 3 is drawn out from the inner case 20. The third inclined surface 514 is inclined toward the −Y direction as a distance from the side plate 23 increases.

=Projecting Portion=

In order to take out the water tray 402 (FIG. 4), an end portion, of the water tray 402, on the side closer (−Y) to the opening 21A is required to be lifted up in such a manner as to become higher in the vertical direction than a part 2D of the gasket 210. For example, in a case where a relatively large amount of water is stored in the water tray 402, the water in the water tray 402 may be spilled out when the end portion of the water tray 402 on a −Y side is abruptly lifted up. Note that the part 2D of the gasket 210 is a part, of the gasket 210, provided on the lower edge of the opening 21A.

A projecting portion 401 is used in taking out the water tray 402 to the outside of the inner case 20 and the outer case 10 through the opening 21A. The projecting portion 401 is formed such that the bottom plate 25 is subject to press working so as to project upward (+Z). The projecting portion 401 is provided closer to the opening 21A (−Y) in the bottom plate 25. The projecting portion 401 is in a long shape continually extending along the X-axis. The projecting portion 401 is in a chevron shape with a predetermined height. The height of the projecting portion 401 is set, at such a height that the water tray 402 can be guided, such that the end portion on the −Y side of the water tray 402 will be positioned higher than the part 2D of the gasket 210 when the water tray 402 is taken out.

When the water tray 402 is taken out, a force toward the opening 21A side (−Y) is exerted on the end portion on the −Y side of the water tray 402. With this force, the water tray 402 is moved from the +Y side to the −Y side. The water tray 402 is guided by the projecting portion 401 such that the position in the vertical direction of the end portion on the −Y side of the water tray 402 becomes higher than the part 2D of the gasket 210, thereby being taken out to the outside of the inner case 20 and the outer case 10. Note that, at this time, the position in the vertical direction of the end portion on the −Y side of the water tray 402 becomes higher in a gradual manner with the guidance of the projecting portion 401, which prevents the water stored in the water tray 402 from being spilled out.

===Side Plate, Gasket===

Figure 18:
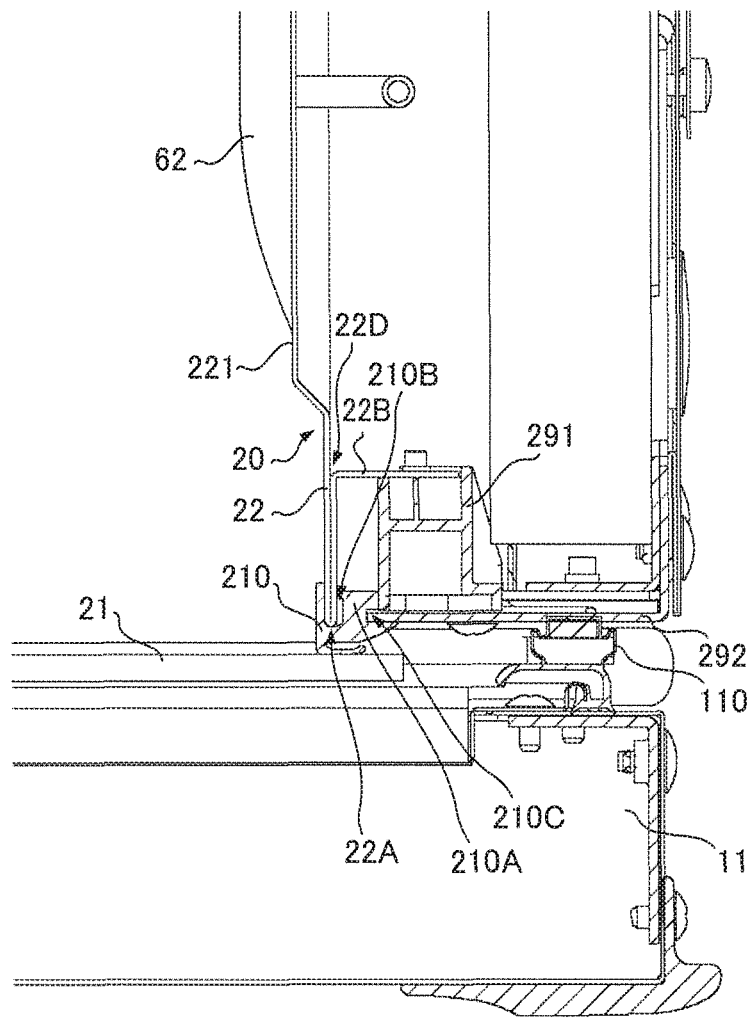
FIG. 18 is a cross-sectional view illustrating a part of the culture apparatus according to the first embodiment.

Hereinafter, the side plate and the gasket according to the present embodiment will be described with reference to FIG. 18. FIG. 18 is a cross-sectional view illustrating a part of the culture apparatus according to the present embodiment. Note that FIG. 18 illustrates, in detail, a part of the culture apparatus 100 on the −Y side and a −X side in FIG. 11, a part of the outer door 11, and a part of the inner door 21.

The side plate 22 of the inner case 20 includes a fixing piece 22B and the aforementioned rising portion 221.

The fixing piece 22B is used to fix the inner case 20 to the outer case 10. The fixing piece 22B is a part, of the side plate 22, that is formed such that the side plate 22 is folded back at a folding-back part 22A and then bent at a bend part 22D. At the folding-back part 22A, an end portion on the −Y side of the side plate 22 is folded back in a counterclockwise direction when viewed from +Z toward −Z with respect to a folding-back line along the Z-axis. At the bend part 22D, the end portion, of the side plate 22, folded back at the folding-back part 22A is bent by substantially 90 degrees in a clockwise direction when viewed from +Z toward −Z with respect to a bending line along the Z-axis. Thus, the fixing piece 22B is provided, in a state substantially parallel to an XZ plane, on the +Y side in Y-axis direction relative to the folding-back part 22A. The fixing piece 22B is fixed to a resin inner-case fixing part 291 using, for example, a bolt, a nut, etc. Note that the rising portion 221 is formed such that an inner face (+X) in the rising portion 221 will be positioned on a +X side, in the X-axis direction, relative to the gasket 210.

The inner-case fixing part 291 is used to fix the inner case 20 to the outer case 10. The inner-case fixing part 291 is provided between the fixing piece 22B and a front plate 292. The inner-case fixing part 291 is further fixed to the front plate 292 using, for example, a bolt, a nut, etc. Note that the front plate 292 is a metal plate forming a front surface in which the opening 21A (FIG. 2) of the outer case 10 is provided. The length in the X-axis direction of the front plate 292 is set such that a space for providing the gasket 210 between the front plate 292 and the folding-back part 22A of the side plate 22 will be formed.

The gasket 210 may be made of, for example, an elastically deformable material such as rubber, etc. The gasket 210 has depressions 210B, 210C for attaching the gasket 210 to the edge of the opening 21A. The depression 210B is depressed from the +Y side toward the −Y side so that the folding-back part 22A of the side plate 22 can be fit. The depression 210C is depressed from the −X side toward the +X side such that an end portion on the +X side of the front plate 292 can be fit. The gasket 210 is fixed to the side plate 22 and the front plate 292, with the folding-back part 22A and the end portion of the front plate 292 being fit into the depressions 210B and 210C, respectively. At this point, a part 210A of the gasket 210 is in a state sandwiched between the front plate 292 and the folding-back part 22A, and thus the gasket 210 is securely fixed to the side plate 22 and the front plate 292.

Further, the gasket 110 of the outer door 11 is provided at such a position, in the outer door 11, as to face the front plate 292. Note that the gasket 110 may be made of a material similar to that of the gasket 210.

===Shelf===

Figure 11:
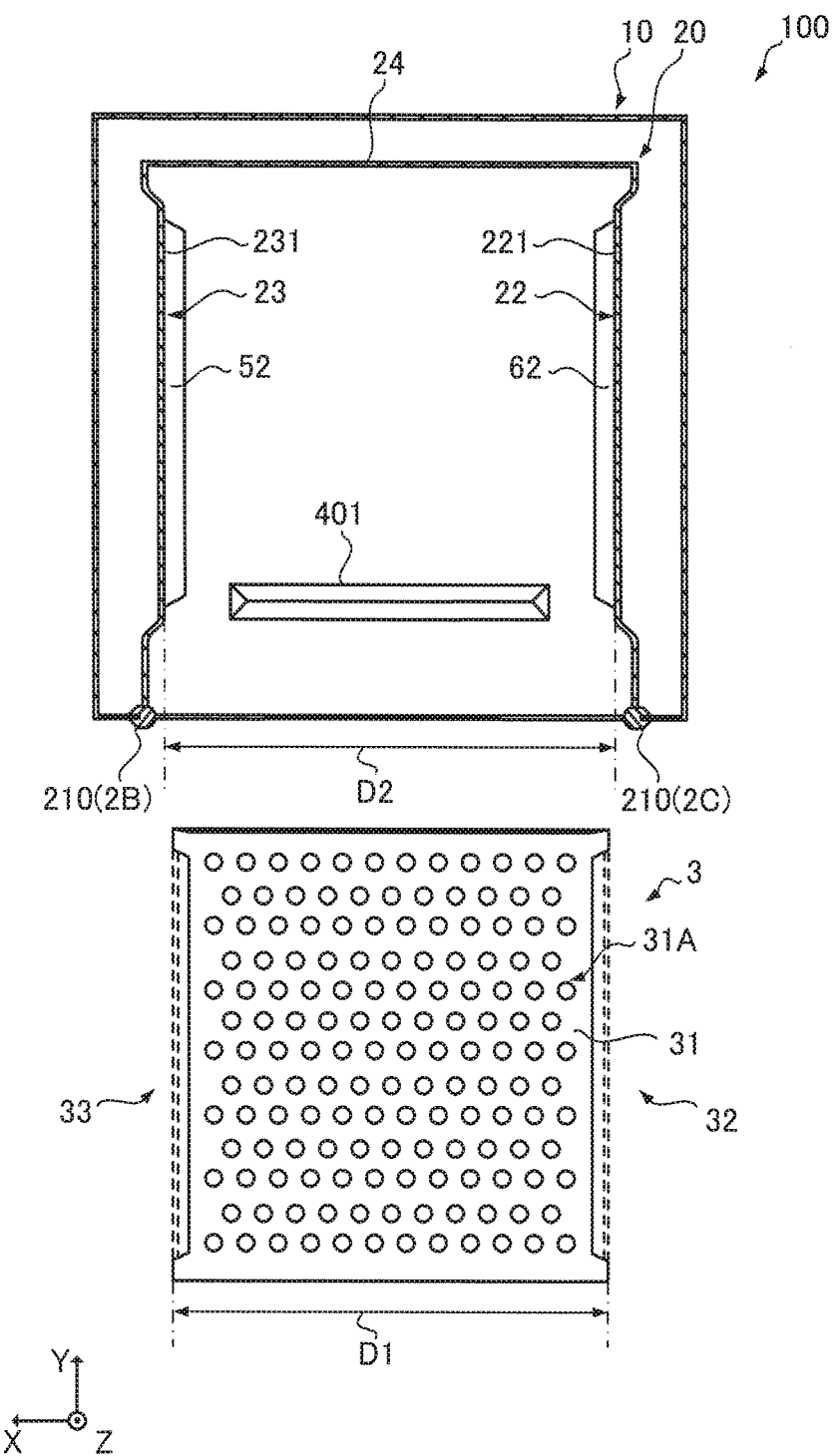
FIG. 11 is a diagram illustrating the culture apparatus and the shelf according to the first embodiment.

Hereinafter, the shelf according to the present embodiment will be described with reference to FIGS. 10 and 11. FIG. 10 is a side view illustrating the shelf rest in a state where the shelf according to the present embodiment is placed thereon. FIG. 11 is a diagram illustrating the culture apparatus and the shelf according to the present embodiment. Note that FIG. 11 illustrates a plan view of the shelf. FIG. 11 further illustrates the culture apparatus 100 when viewed toward the −Z direction from a cross-section, parallel to the XY plane passing between the shelf rests 51 and 52 in the vertical direction (Z-axis) in FIG. 5.

The shelf 3 (FIG. 11) is in a shape symmetrical with respect to a symmetry plane, parallel to the YZ plane, passing through substantially the center of the shelf 3. The shelf 3 includes the bottom plate 31 and side parts 32, 33, and is integrally formed by folding a single metal plate.

The bottom plate 31 is a flat plate substantially in a rectangular shape. The bottom plate 31 includes a plurality of punched holes 31A for circulating the gas in the culture chamber 2A. A width D1 in the X-axis direction of the bottom plate 31 is set narrower than a width D2 in the X-axis direction from the rising portion 231 on the −X side to the rising portion 221 of the side plate 22. Accordingly, when the shelf 3 is placed on the shelf rest 52, a space D33 is formed between a first bent segment 331 and the rising portion 231, as well as a space similar to the space D33 is also formed between a first bent piece of the side part 32 and the rising portion 221. Since the side parts 32, 33 have constructions similar to each other, only the side part 33 will be described, and the description of the construction of the side part 32 is omitted. The side part 33 includes the first bent segment 331 (FIG. 10) and a second bent segment 332.

The first bent segment 331 is bent upward (+Z) from an end on the +X side of the bottom plate 31. The first bent segment 331 is bent such that the curvature of a bend 333 becomes greater than the curvature of a bend 521A which continues from a surface (−X) on the culture chamber 2A side in the rising portion 231 to a placement surface 521. The length in the vertical direction (Z-axis) of the first bent segment 331 is set shorter than the distance in the vertical direction from the placement surface 521 to the first inclined surface 512.

The second bent segment 332 is further bent from the first bent segment 331. The second bent segment 332 is bent from an upper end portion in the first bent segment 331 toward the center (−X) of the inner case 20. The second bent segment 332 is bent along the first inclined surface 512 of the stopper 51A and a first inclined surface 516 of the stopper 51B.

===Moving in and Out of Shelf===

Figure 12:
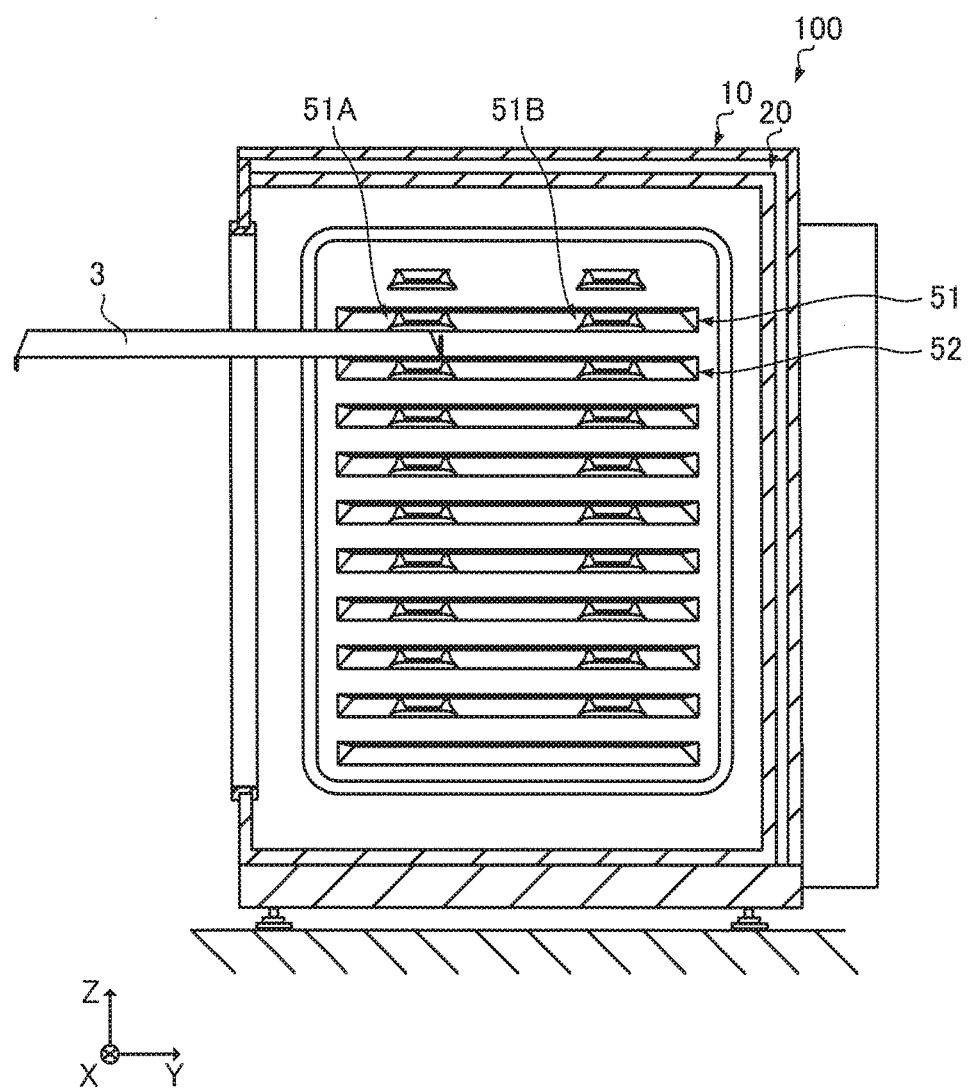
FIG. 12 is a side view illustrating the shelf and the culture apparatus according to the first embodiment.

Hereinafter, moving in and out of the shelf according to the present embodiment will be described with reference to FIGS. 2, 10, and 12. FIG. 12 is a side view illustrating the shelf and the culture apparatus according to the present embodiment. Note that the side plates 22, 12 of the culture apparatus 100 are omitted for explanation's sake.

=When Inserting Shelf=

The outer door 11 and the inner door 21 are opened to bring a state where the shelf 3 can be inserted into the inner case 20 through the opening 21A.

The shelf 3 is moved from the front side (−Y) toward the back side (+Y), for example, between the shelf rests 52, 62 and the shelf rests 51, 61, in such a manner as to be placed on the shelf rests 52, 62. At this time, the movement of the side part 33 is guided by the placement surface 521 located lower (−Z) than the shelf 3 (FIG. 10) and the inclined surface 515 located above the shelf 3. Note that the inclination of the second inclined surface 513 of the stopper 51A prevents the shelf 3 from being blocked by the stopper 51A. Note that the side part 32 is guided similarly to the side part 33. Further, in the X-axis direction, the movement of the shelf 3 is guided, with the internal surface (−X) of the rising portion 231 and the internal surface (+X) of the rising portion 221 coming into contact with the side parts 33, 32 of the shelf 3, respectively.

The shelf 3 is moved inside the inner case 20, to be placed on the shelf rests 52, 62. At this point, since the placement surface 521 is inclined, the side part 33 of the shelf 3 comes in line contact with the shelf rest 52. Thus, it becomes possible to fill the culture chamber 2A with sterilizing gas, to reliably sterilize the interior of the inner case 20. Note that the side part 32 also comes into line contact with the shelf rest 62, similarly to the side part 33.

Note that the curvature of the bend 333 in the side part 33 is set greater than the curvature of the bend 521A. The shelf 3 slides down the placement surface 521 in such a manner as to be positioned at the predetermined location, and thus the positioning of the shelf 3 in the X-axis direction is reliably performed.

After the shelf 3 is inserted, the inner door 21 and the outer door 11 are closed.

=When Drawing Out Shelf=

The outer door 11 and the inner door 21 are opened to bring a state where the shelf 3 in the inner case 20 can be drawn out through the opening 21A.

The shelf 3 placed on the shelf rests 52, 62 is moved from the back side toward the front side. The movement thereof in the vertical direction is limited by the stoppers 51A and 52A, and thus, for example, the shelf 3 can be prevented from being inclined to fall off during its movement. Note that the shelf 3 being inclined indicates that the front end portion of the shelf 3 is lower or higher than the back end portion. Further, the side part 33 in the shelf 3 comes into contact with the first inclined surfaces 512, 516 of the stoppers 51A, 51B provided to the upper shelf rest 51, which prevent an angle of lateral inclination of the shelf 3 from further increasing, thereby reliably preventing the shelf 3 from falling off. Note that the second bent segment 332 of the shelf 3 is formed along the first inclined surfaces 512, 516, which prevents, for example, the side part 33 and the first inclined surfaces 512, 516 from being partially shaved to generate dust, when the second bent segment 332 comes into contact with the first inclined surfaces 512, 516.

After the shelf 3 is drawn out, the inner door 21 and the outer door 11 are closed.

Second Embodiment

Figure 13:
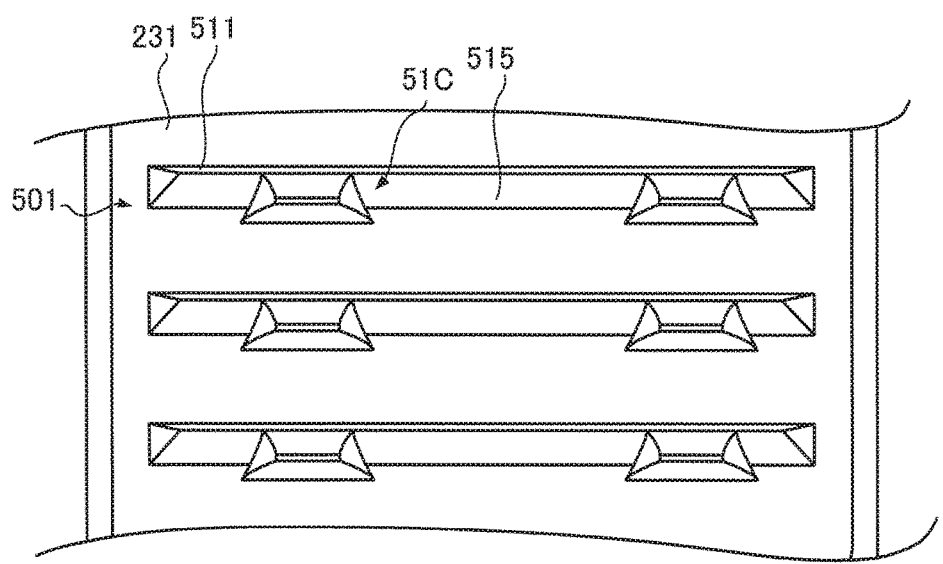
FIG. 13 is a front view illustrating shelf rests according to a second embodiment.
Figure 13:
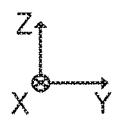

In a culture apparatus 100B (FIG. 1) according to a present embodiment, each shelf rest in the plurality of shelf rests 5, 6 is altered into a shelf rest 501 (FIG. 13). The structure of the culture apparatus 100B, except the shelf rest 501, is similar to that of the culture apparatus 100.

===Shelf Rest===

Hereinafter, the shelf rest according to the present embodiment will be described with reference to FIG. 13. FIG. 13 is a front view illustrating the shelf rest according to the present embodiment. Note that the components similar to those in FIG. 8 are designated by the same reference numerals, and the descriptions thereof are omitted.

In the shelf rest 501, the stoppers 51A, 51B of the shelf rest 51 (first embodiment) are altered into stoppers 51C. The construction of the shelf rest 501, except the stoppers 51C, is similar to that of the shelf rest 51. The stoppers 51C are provided extending between the inclined surface 515 and the rising portion 231, of the side plate 23 in the inner case 20, continued downward (−Z) from the inclined surface 515.

Third Embodiment

Figure 14:
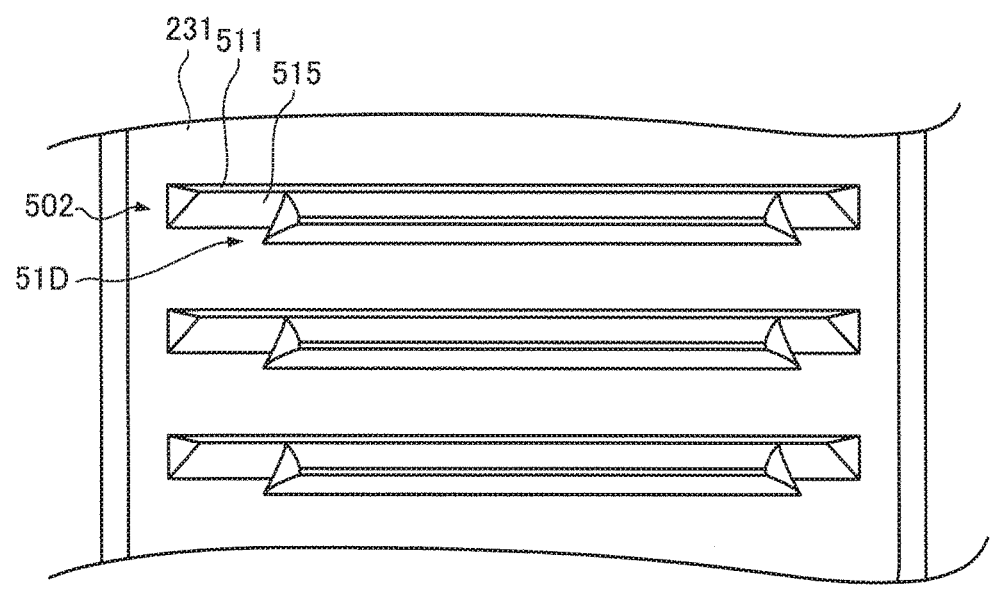
FIG. 14 is a front view illustrating shelf rests according to a third embodiment.

In a culture apparatus 100C (FIG. 1) according to a present embodiment, each shelf rest of the plurality of shelf rests 5, 6 is altered into a shelf rest 502 (FIG. 14). The structure of the culture apparatus 100C, except the shelf rest 502, is similar to that of the culture apparatus 100.

===Shelf Rest===

Hereinafter, the shelf rest according to the present embodiment will be described with reference to FIG. 14. FIG. 14 is a front view illustrating the shelf rest according to the present embodiment. Note that components similar to those in FIG. 8 are designated by the same reference numerals, and the descriptions thereof are omitted.

In the shelf rest 502, the stoppers 51A, 51B of the shelf rest 51 (first embodiment) are altered into a stopper 51D. The construction of the shelf rest 502, except the stopper 51D, is similar to that of the shelf rest 51. The stopper 51D is provided extending between the inclined surface 515 and the rising portion 231, of the side plate 23 in the inner case 20, continued downward (−Z) from the inclined surface 515. The stopper 51D is provided along the longitudinal direction (Y-axis) of the shelf rest 502, and is in a long shape. The length in the longitudinal direction of the stopper 51D is set shorter than the length in the longitudinal direction of the shelf rest 502. Note that, for example, the length in the longitudinal direction of the stopper 51D may be set longer than the length in the longitudinal direction of the shelf rest 502, and also may be set to substantially the same length as that in the longitudinal direction of the shelf rest 502. Further, the stopper 51D may be provided only to the inclined surface 515.

As described above, the culture apparatus 100 (first embodiment) is a device configured to cultivate a culture inside the inner case 20. The culture apparatus 100 includes the outer case 10; the inner case 20; the outer door 11; and the inner door 21. The inner case 20 is configured with the metal plates 72, 73, 75, 76, etc., arranged inside the outer case 10. The outer door 11 and the inner door 21 are configured to open/close the opening 21A. On the side plates 22, 23 of the inner case 20, the shelf rests 5, 6 are formed by press working, and the side parts 32, 33 on both sides of the bottom plate 31 (bottom surface) of the shelf 3, where the culture is to be placed, are to be placed on the shelf rests 5, 6. On the side plate 23, further, stoppers 51A, 51B are formed by press working. Note that, on the side plate 22 as well, stoppers having construction similar to that of the stopper 51A are formed. The stopper 51A and the like are provided in order that the upper shelf rest 51 may limit the movement in the vertical direction of the shelf 3 placed on the immediately lower shelf rest 52, the upper and lower shelf rests, 51, 52 being immediately adjacent to each other in the vertical direction. Thus, supports, etc., for supporting the shelf 3 are not provided inside the inner case 20, which facilitates cleaning of the interior of the inner case 20. Further, supports, etc., for supporting the shelf 3 are not required to be provided inside the inner case 20, which enables reduction in the number of components of the culture apparatus 100, thereby enabling reduction in the manufacturing costs of the culture apparatus 100. Further, for example, the stopper 51A and the like can prevent the shelf 3 placed on the lower shelf rest 52 from being inclined to fall off, when the shelf 3 is being drawn out from the inner case 20. Therefore, the culture apparatus 100 with high usability, which is capable of preventing the shelf 3 from being inclined to fall off, can be provided. Further, it becomes possible to provide the plurality of shelves 3 in the vertical direction. Thus, with adjustment of the number of the shelves 3 which are to be provided inside the inner case 20, a distance between the shelves 3 immediately adjacent to each other in the vertical direction can be adjusted. Accordingly, the culture apparatus 100 with high usability can be provided.

Further, the shelf rest 51 includes: the placement surface 511 on which the shelf is to be placed; and the inclined surface 515 formed on the underside of the placement surface 511. The stopper 51A is provided, at a position below the placement surface 511, to the inclined surface 515. The stopper 51A is provided to the shelf rest 51 in an integral manner. Thus, for example, it can be prevented that the shelf 3 gets caught between the upper shelf rest 51 and the stopper 51A, when the shelf 3 is placed on the shelf rest 52. Further, on such an occasion, the stopper 51A performs a function, as a guide, of guiding the shelf 3 to the interior of the inner case 20, together with the upper shelf rest 51.

Thus, the culture apparatus 100 with high usability can be provided, preventing that the shelf 3 get caught when the shelf 3 is being provided inside the inner case 20.

Further, the stoppers 51C (FIG. 13) are provided extending between the inclined surface 515 and the rising portion 231, of the side plate 23 in the inner case 20, continued downward from the inclined surface 515. With this construction, the stopper 51C can be positioned closer to the shelf rest 52 located below the stopper 51C. Thus, it becomes possible to limit the movement in the vertical direction of the shelf 3 provided inside the inner case 20, thereby being able to reliably prevent the shelf 3 from falling off.

Further, the shelf rest 51 is in a long shape. The stoppers 51A, 51B are provided to the shelf rest 51, in a plural manner along the longitudinal direction of the shelf rest 51. With this construction, it becomes possible, for example, to reliably prevent the shelf 3 from falling off when the shelf 3 placed on the shelf 52 from being moved to the +Y-side or the −Y-side.

Further, the inner case 20 is in a rectangular parallelepiped shape including the top plate 26, the side plates 22, 23, the bottom plate 25, and the back plate 24. The top plate 26 and the side plates 22, 23 are welded together such that joint positions 721, 731 (FIG. 6) are located closer to the side plates 22, 23 with respect to the corner parts 201, 202 of the rectangular parallelepiped shape, respectively. The bottom plate 25 and the side plates 22, 23 are welded together such that the joint positions 722, 732 are located closer to the side plates 22, 23 with respect to the corner parts 203, 204 of the rectangular parallelepiped shape, respectively. Further, as will be described later, the top plate 26 and the side plates 22, 23 are welded together such that joint positions 761, 762 (FIG. 15) are located closer to the top plate 26 with respect to the corner parts 201, 202 of the rectangular parallelepiped shape, respectively. The bottom plate 25 and the side plates 22, 23 are welded together such that joint positions 751, 752 are located closer to the bottom plate 25 with respect to the corner parts 203, 204 of the rectangular parallelepiped shape, respectively. Thus, since the joint positions are located away from the corner parts, the culture apparatus 100, in which the corner parts of the inner case 20 can be reliably cleaned, can be provided.

Note that the above first to third embodiments are simply for facilitating the understanding of the present disclosure and are not in any way to be construed as limiting the present disclosure. The present disclosure may variously be changed or altered without departing from its spirit and encompass equivalents thereof.

In the first embodiment, it has been described that two stoppers, which are the stoppers 51A, 51B, are provided in the longitudinal direction (Y-axis) of the shelf rest 51, but it is not limited thereto. For example, a single stopper whose structure is similar to that of the stopper 51A may be provided to the shelf rest 51 in the longitudinal direction, or three stoppers or more may be provided thereto.

Figure 15:
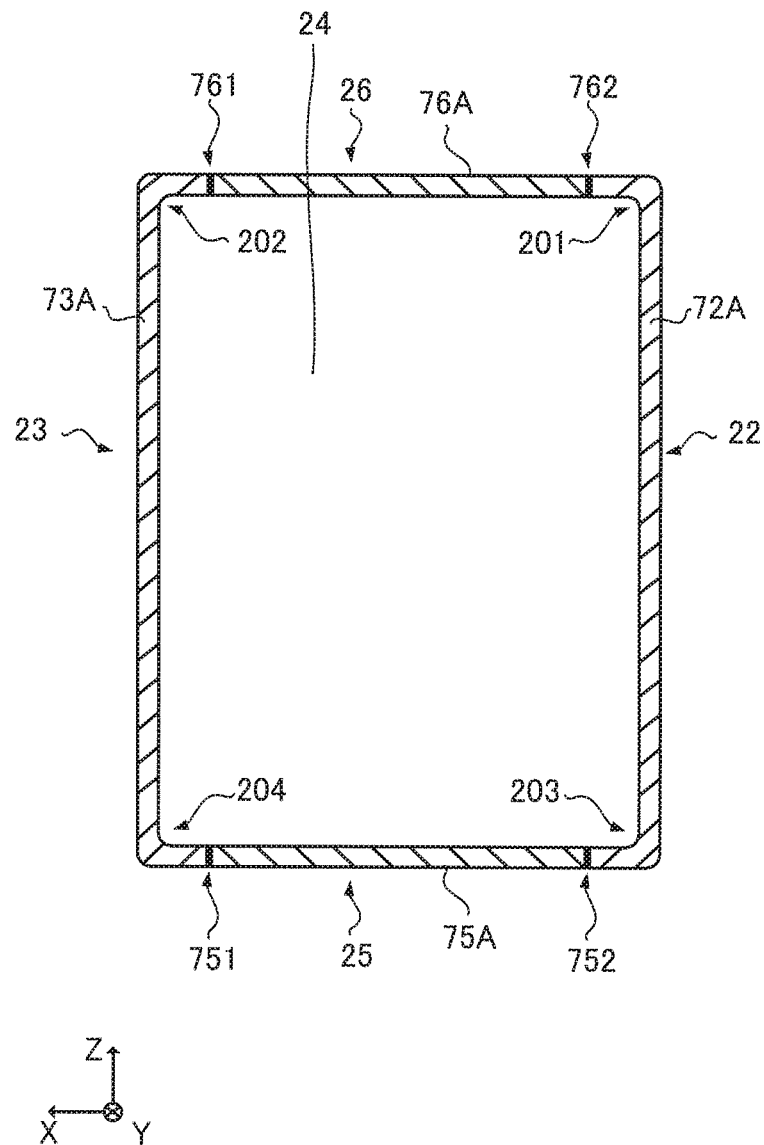
FIG. 15 is a cross-sectional view illustrating the inner case.

Further, in the first embodiment, it has been described that the inner case 20 is formed such that the joint parts 721, 731 are located closer to the side plates 22, 23 with respect to the corner parts 201, 202 of the inner case 20, respectively, and the joint parts 722, 732 are located closer to the side plates 22, 23 with respect to the corner parts 203, 204 of the inner case 20, respectively, but it is not limited thereto. For example, the inner case 20 may be formed as illustrated in FIG. 15. FIG. 15 is a cross-sectional view illustrating the inner case. Note that the components similar to those in FIG. 6 are designated by the same reference numerals, and the descriptions thereof are omitted.

The side plates 22, 23, the bottom plate 25, and the top plate 26 are formed such that four metal plates 72A, 73A, 75A, and 76A are welded together. The metal plate 76A is a plate member to form the top plate 26. The metal plate 75A is a plate member to form the bottom plate 25. The metal plates 72A, 73A are plate members to form the side plates 22, 23. The both ends of the metal plate 72A are bent such that the joint part 762 is located closer to the top plate 26 with respect to the corner part 201, and the joint part 752 is closer to the bottom plate 25 with respect to the corner part 203. The both ends of the metal plate 73A are bent such that the joint part 761 is located closer to the top plate 26 with respect to the corner part 202 and the joint part 751 is located closer to the bottom plate 25 with respect to the corner part 204.

The ends of the metal plate 72A are welded to one ends (−X) of the metal plates 76A, 75A, at joint parts 762, 752, respectively. The ends of the metal plate 73A are welded to the other ends (+X) of the metal plate 72A, 73A, at the joint parts 761, 751, respectively. The back surface plate 24 is welded to the edges on the +Y side of the metal plates 72A, 73A, 75A, and 76A. Accordingly, the inner case 20 is formed.

Further, for example, only the lower end (−Z) of the metal plate 72A may be bent such that the joint part 762 is located closer to the side plate 22, and the joint part 752 is located closer to the bottom plate 25. Also, only the upper end (+Z) thereof may be bent such that the joint part 762 is located closer to the top plate 26, and the joint part 752 is located closer to the side plate 22. Further, only either one of the upper end and the lower end of the metal plate 73A may be bent, similarly to the metal plate 72A.

Figure 16:
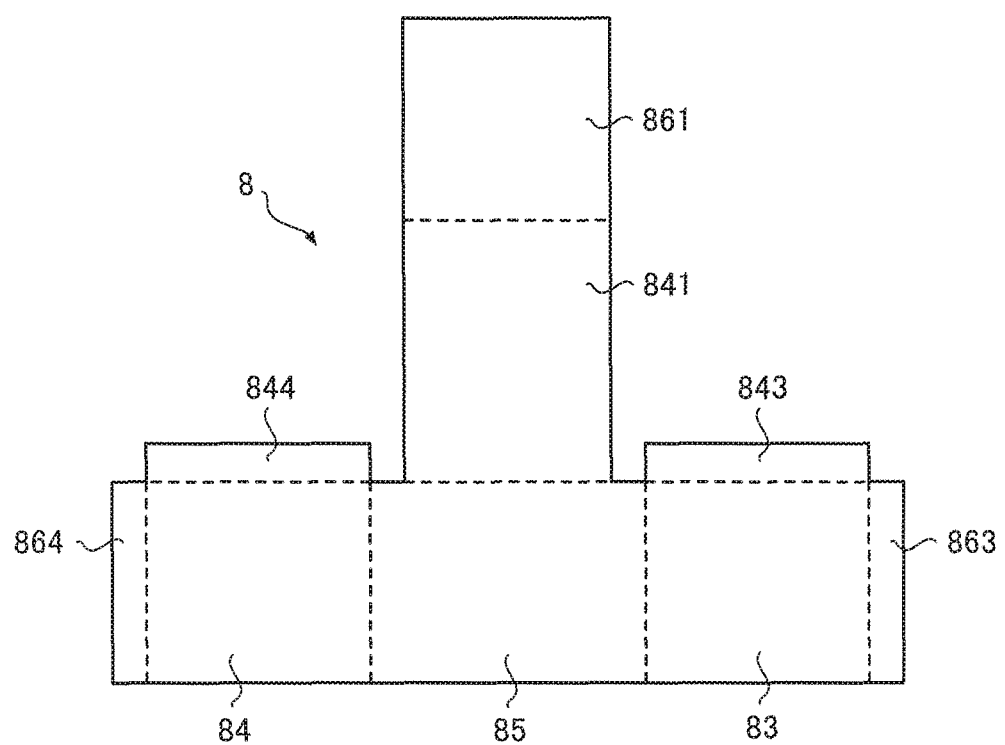
FIG. 16 is a diagram illustrating a metal plate for forming an inner case.
Figure 17:
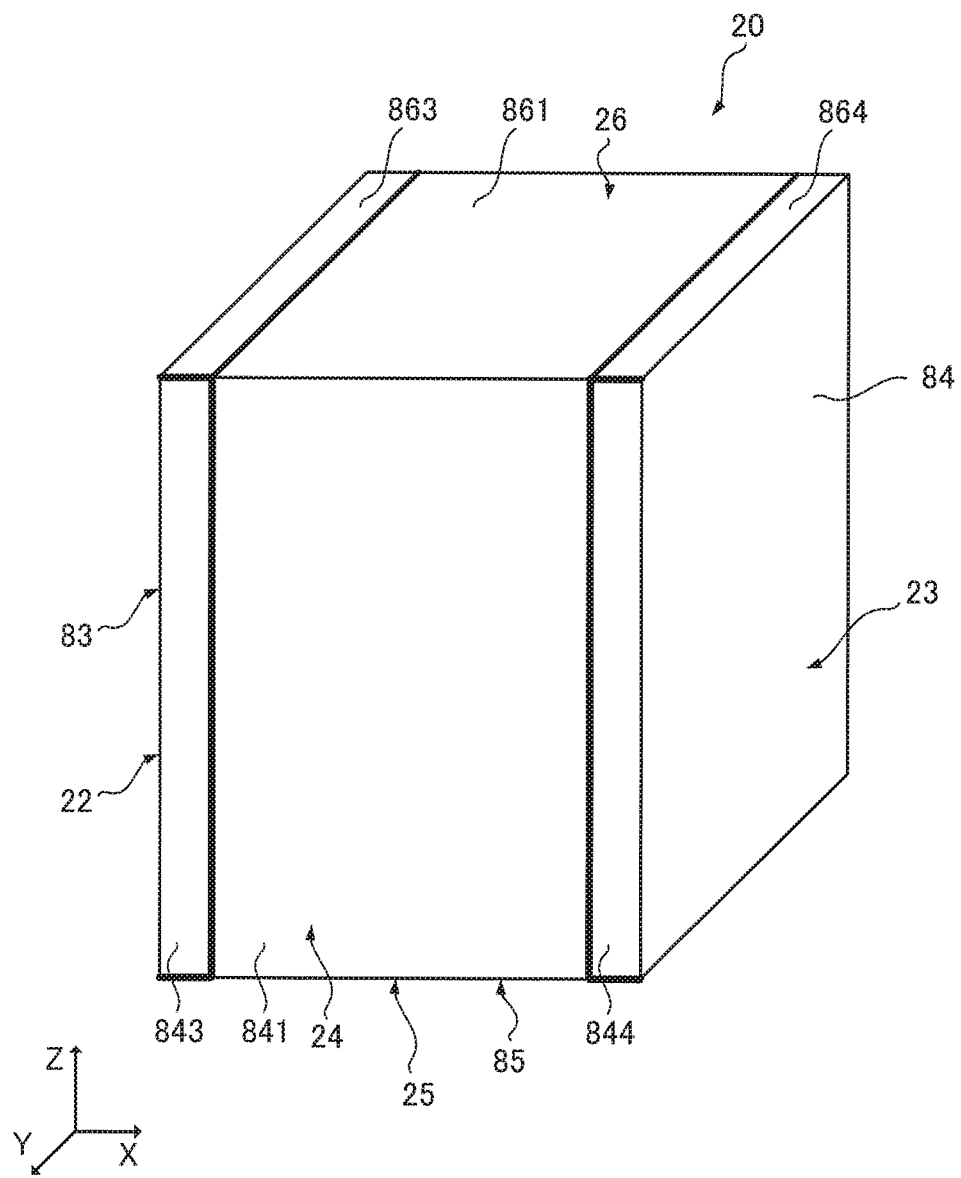
FIG. 17 is a perspective view illustrating the inner case.

Further, in the first embodiment, it has been described that the four metal plates 72, 73, 75, and 76 are welded together to form the inner case 20, but it is not limited thereto. For example, a single metal plate 8 (FIG. 16) may be subject to bending work and welded to form the inner case 20 (FIG. 17). FIG. 16 is a diagram illustrating the metal plate to form an inner case. FIG. 17 is a perspective view illustrating the inner case. The metal plate 8 is, for example, mountain-folded by substantially 90 degrees at broken lines illustrated in FIG. 16. Thereafter, the sides adjacent to each other in the folded metal plate 8 are welded together, to form the inner case 20. Note that, in the metal plate 8, a first part 83 corresponds to the side plate 22, a second part 84 corresponds to the side plate 23, a third part 85 corresponds to the bottom plate 25, and fourth parts 841, 843, 844 correspond to the back plate 24, and a fifth parts 861, 863, 864 correspond to the top plate 26.

Further, in the first embodiment, it has been described that the first bent segment 331 is bent such that the curvature of the bend 333 (FIG. 10) becomes greater than the curvature of the bend 521A, but it is not limited thereto. For example, the first bent segment 331 may be bent such that the curvature of the bend 333 becomes less than the curvature of the bend 521A. In this case, a space is formed between the side part 33 of the shelf 3 placed on the placement surface 521 and, the rising portion 231 and placement surface 521. This enables sterilizing gas in the culture chamber 2A to be introduced into this space, thereby being able to reliably sterilize the inside of the culture chamber 2A.

Further, in the first embodiment, it has been described that the projecting portion 401 (FIG. 4) is in a long shape continued along the X-axis, but it is not limited thereto. For example, a plurality of projections having a function similar to that of the projecting portion 401 may be provided along the X-axis, and also a single projection in the plurality of projections may be provided.

Further, in the first embodiment, it has been described that a single metal plate is folded to integrally form the shelf 3, but it is not limited thereto. For example, the side parts 32, 33 may be welded to the bottom plate 31, to from the shelf 3.

REFERENCE SIGNS LIST 3 shelf
5, 6 a plurality of shelf rests
10 outer case
11 outer door
12, 13, 22, 23 side plate
14, 24 back plate
15, 25, 31 bottom plate
16, 26 top plate
20 inner case
21 inner door
32, 33 side part
51 to 59, 61 to 69, 501, 502 shelf rest
51A, 51B, 51C, 51D stopper
100, 100B, 100C culture apparatus

What is claimed is:

1. A culture apparatus configured to cultivate cultures, the culture apparatus comprising:
an outer case;
an inner case configured with two side plates, a bottom plate and a top plate, all of which are metal plates, the inner case being arranged inside the outer case;
a door configured to open and close an opening formed in a front face of the inner case; and
a plurality of shelves on which the cultures are to be placed, wherein:
the side plates include plural pairs of shelf rests formed by press working, each of the plural pairs of shelf rests includes stoppers formed by press working,
each of the plurality of shelves includes side parts on both sides of bottom surfaces, the side parts being configured to be placed on one of the pairs of shelf rests in such a manner that the plurality of shelves are arranged in a vertical direction,
the stoppers are provided such that the stoppers of one pair of shelf rests limit movement in a vertical direction of a shelf placed on an immediately lower pair of shelf rests,
each of the plurality of shelf rests includes a placement surface, on which one of the shelves is to be placed, and an inclined surface formed on undersides of the placement surface, and
the stoppers are provided, below the placement surface, on the inclined surface, and include a first inclined surface and a second inclined surface,
the first inclined surface being lower than the inclined surface and the second inclined surface extending laterally towards the opening as a distance from the corresponding side plate increases.

2. The culture apparatus according to claim 1, wherein each of the stoppers extends between the inclined surface and a part of one of the side plates of the inner case.

3. The culture apparatus according to claim 1, wherein:
each of the plurality of shelf rests is in a long shape, and
the stoppers are provided to each of the plurality of shelf rests, along respective longitudinal directions of the plurality of shelf rests.

4. The culture apparatus according to claim 2, wherein each of the plurality of shelf rests is in a long shape, and
the stoppers are provided to each of the plurality of shelf rests, along respective longitudinal directions of the plurality of shelf rests.

5. The culture apparatus according to claim 1, wherein:
the inner case is in a rectangular parallelepiped shape configured with the top plate, the side plates on both sides, the bottom plate, and a back plate,
the top plate and the side plates are welded together such that their joint positions are offset from corners of the rectangular parallelepiped shape, and
the bottom plate and the side plates are welded together such that their joint positions are offset from corners of the rectangular parallelepiped shape.

6. The culture apparatus according to claim 2, wherein the inner case is in a rectangular parallelepiped shape configured with the top plate, the side plates on both sides, the bottom plate, and a back plate,
the top plate and the side plates are welded together such that their joint positions are offset from corners of the rectangular parallelepiped shape, and
the bottom plate and the side plates are welded together such that their joint positions are offset from corners of the rectangular parallelepiped shape.

7. The culture apparatus according to claim 3, wherein the inner case is in a rectangular parallelepiped shape configured with a top plate, side plates on both sides, a bottom plate, and a back plate,
the top plate and the side plates are welded together such that their joint positions are closer to the top plate or the side plates than corner parts of the rectangular parallelepiped shape, and
the bottom plate and the side plates are welded together such that their joint positions are closer to the bottom plate or the side plates than to corner parts of the rectangular parallelepiped shape.

8. The culture apparatus according to claim 4, wherein the inner case is in a rectangular parallelepiped shape configured with a top plate, side plates on both sides, a bottom plate, and a back plate,
the top plate and the side plates are welded together such that their joint positions are closer to the top plate or the side plates than to corner parts of the rectangular parallelepiped shape, and
the bottom plate and the side plates are welded together such that their joint positions are closer to the bottom plate or the side plates than to corner parts of the rectangular parallelepiped shape.

9. A culture apparatus configured to cultivate cultures, the culture apparatus comprising:
an outer case;
an inner case configured with a left side plate, a right side plate, a bottom plate and a top plate, all of which are metal plates, the inner case being arranged inside the outer case;
a door configured to open and close an opening formed in a front face of the inner case; and
a plurality of shelves on which the cultures are to be placed, wherein:
each of the left and right side plates has a rising portion on which shelf rests are disposed,
one of the shelf rests formed on the left side plate and corresponding one of the shelf rests formed on the right side plate constitute a pair of shelf rests, on which side ends of a bottom surface of one of the plurality of shelfs are to be placed, each of the pair of shelf rests includes an upper face as a placement portion, on which one of the plurality of shelves is to be placed, and a lower face, and
a stopper portion which limits movement in a vertical direction of a shelf placed on an immediately lower pair of shelf rests is provided on the lower face and protrudes from the lower face by the press working,
the stopper portion includes a first inclined surface and a second inclined surface,
the first inclined surface being lower than the inclined surface and the second inclined surface extending laterally towards the opening as a distance from the corresponding side plate increases.

10. The culture apparatus according to claim 9, wherein plural stopper portions are provided to one shelf rest.

11. The culture apparatus according to claim 9, wherein a bottommost portion of the stopper portion is located lower than a bottommost portion of the lower face.

12. The culture apparatus according to claim 9, wherein a bottommost shelf rest among the shelf rests does not have a stopper portion.

\* \* \* \* \*